United States Patent [19]

Mitchell

[11] Patent Number: 5,085,510
[45] Date of Patent: Feb. 4, 1992

[54] PHARMACEUTICAL TABLET VISION INSPECTION SYSTEM

[75] Inventor: William H. Mitchell, Cranford, N.J.

[73] Assignee: Pfizer Inc., New York, N.Y.

[21] Appl. No.: 574,166

[22] Filed: Aug. 28, 1990

[51] Int. Cl.⁵ .............................................. H04N 7/18
[52] U.S. Cl. .................................... 356/237; 356/394; 209/577; 358/106
[58] Field of Search .............................. 356/237, 394; 250/223 R; 358/106; 209/577, 587

[56] References Cited

U.S. PATENT DOCUMENTS

| | | | |
|---|---|---|---|
| 4,319,269 | 3/1982 | Kajiura et al. | 358/106 |
| 4,354,602 | 10/1982 | Miyushi et al. | 250/223 R |
| 4,644,150 | 2/1987 | Kuga et al. | 356/237 |
| 4,757,382 | 7/1988 | Kaziura et al. | 358/101 |

OTHER PUBLICATIONS

Kanebo Engineering Co., Ltd., Manufacturer, Osaka 530, Japan, "Medical Tablets Video Inspecting System, Model TVIS-XX ; Model TVIS-3." (no date).
Kajiura, T., "Automating Video Tablet Inspection," Pharmaceutical Technology, Apr., 1989, pp. 36, 38, 40, 44, 46 and 48.

Primary Examiner—Richard A. Rosenberger
Attorney, Agent, or Firm—Peter C. Richardson; J. Trevor Lumb; A. Dean Olson

[57] ABSTRACT

A visual inspection system for inspecting pharmaceutical tablets. The system comprises a photoelectric detection means for detecting the light intensity within an inspection area on a tablet and for generating a detection signal which varies with that light intensity. The system also comprises a signal processing means for comparing the detection signal to a predetermined standard in order to generate a selection signal and a transducer means which is responsive to the selection signal. A separation means separates the tablets into at least two groups in accordance with the selection signal. Yet another aspect of this invention is a method for inspecting the surface of pharmaceutical tablets using the above-described vision inspection system.

7 Claims, 2 Drawing Sheets

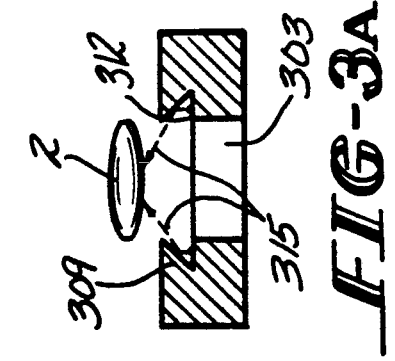
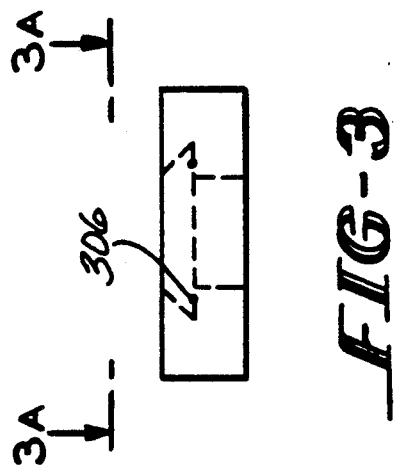
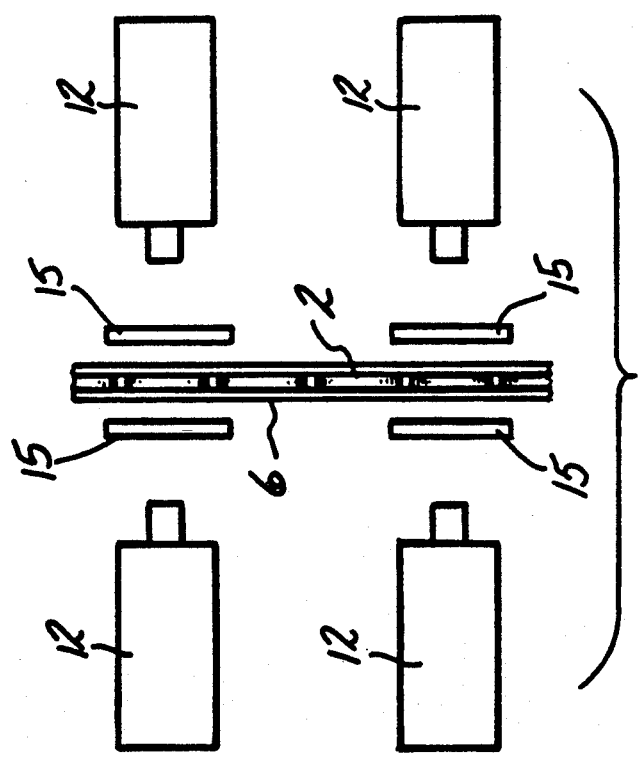

PHARMACEUTICAL TABLET VISION INSPECTION SYSTEM

TECHNICAL FIELD

This invention relates to vision systems for inspecting pharmaceutical tablets and methods for using the same.

BACKGROUND OF THE INVENTION

Traditionally, quality control in the pharmaceutical industry has related to the type, purity, and amount of tablet ingredients. However, quality also relates to defects which can be detected by visual inspection such as dirt, surface blemishes, and surface chips. Although many visual inspections can be performed by operators, manual inspection can be slow, expensive and subject to operator error. Thus, automated vision systems for quality control in the pharmaceutical industry are extremely important.

One such vision system automatically inspects the surface of pharmaceutical tablets and separates the tablets based on predetermined parameters. The system uses a plurality of charge couple device (CCD) high resolution line (one dimensional) sensor cameras to inspect the surfaces of a tablet. In this system tablets stored in a hopper are fed by a vibratory feeder to a flow-control turntable, where they are aligned and proceed to a suction belt system. The suction belt system carries the tablets past a series of line sensor CCD cameras which sequentially inspect the perimeter, the top, and the bottom of each individual tablet. The images are converted into video electronic signals. The signals are differentiated in order to obtain a pattern. The pattern is then compared with the corresponding number of differentiated peaks from a satisfactory tablet, and the defective tablets are identified. Defective tablets are rejected by a pneumatic selector and satisfactory tablets are retained. This particular system is manufactured by Kanebo Engineering (Osaka, Japan).

One recent type of drug delivery device (tablet) contains the active ingredient surrounded by a semipermeable membrane. The semipermeable membrane is permeable to water but impermeable to the active ingredient. The device also includes a substance that swells upon the absorption of water. A coating surrounds the device and a small hole is provided through both the coating and semipermeable membrane, providing a release path for the active ingredient. In use, water passes through the semipermeable membrane, swells the absorptive substance pushing the active ingredient through the hole into the use environment. Since the presence of the hole is important to the intended functioning of the device, verification of the hole presence is equally important. One verification procedure utilizes a beam splitter which checks the discharge intensity of the laser beam used to drill the hole. This is an indirect procedure that merely verifies that the laser was discharged.

Although the above systems provide solutions for automating the inspection of pharmaceutical tablets, there is continual search in this field of art for alternative automated vision inspection systems.

SUMMARY OF THE INVENTION

This invention is directed to a visual inspection system particularly adapted for inspecting pharmaceutical tablets. The system comprises photoelectric detection means for detecting the light intensity within a predetermined inspection area on a tablet and for generating a detection signal which varies with the light intensity. A signal processing means compares the detection signal to a predetermined standard to generate a selection signal. A transducer means is responsive to the selection signal and a separation means for separating the tablets into at least two groups is responsive to the transducer means.

Another aspect of this invention is directed to a method for inspecting the surface of pharmaceutical tablets. The method comprises detecting the light intensity on a tablet with a photoelectric detection means, generating a detection signal which varies with the detected light intensity and comparing the detection signal to a predetermined standard. A selection signal based on the comparison is generated and the tablets are separated into groups in accordance with the selection signal.

Other features and advantages will be apparent from the specification and claims and from the accompanying drawings which illustrate an embodiment of this invention.

BRIEF DESCRIPTION OF DRAWINGS

FIG. 2 illustrates a schematic top view of the exemplary vision inspection apparatus depicted in FIG. 1.

FIG. 3 illustrates a side view of an exemplary lighting head used in the apparatus of FIG. 1.

FIG. 3A illustrates a cross-section taken along line 3A—3A of the lighting head of FIG. 3.

FIG. 4 illustrates a schematic view of the vision inspection process of this invention.

DETAILED DESCRIPTION OF THE INVENTION

Figure 1:
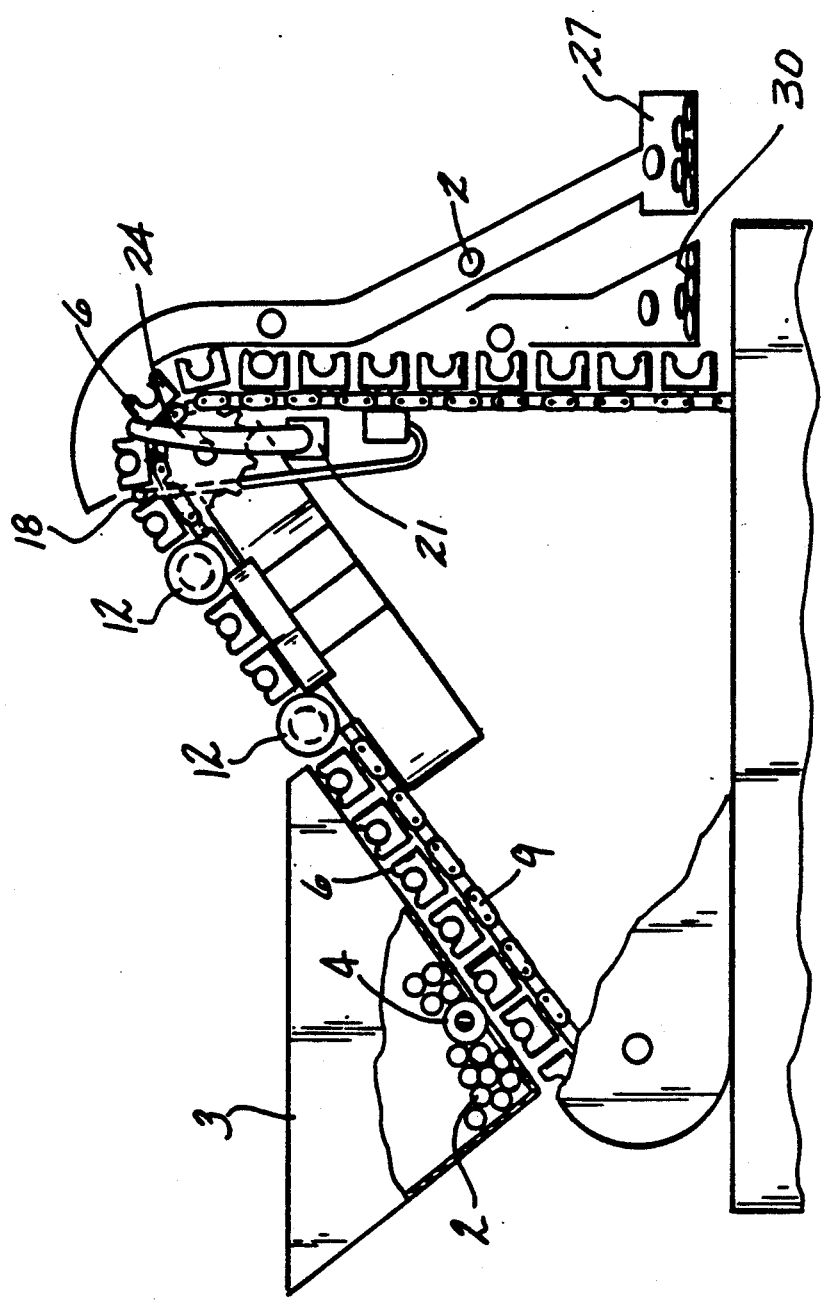
FIG. 1 illustrates a s view of an exemplary vision inspection apparatus of this invention.

According to FIG. 1 hopper 3 is a storage reservoir for the tablets 2 to be inspected. The tablets 2 are dispensed from the hopper 3 and urged into the individual tablet carriers 6 by a pair of spaced apart slowly turning spindles 4 disposed at the bottom of the hopper 3 and above and on either side of the carriers 6. Suitable tablet carriers 6 are available from Alza Inc. (Palo Alto, Cal.). The carriers 6 hold the tablets 2 around the rim in a vertical position so that the tablets 2 are visible from either side. The carriers 6 are connected to a conveyor belt 9 driven by a suitable motor. A suitable conveyor system for transport of the tablets 2 is a Hartnett Delta Printer (R. W. Hartnett Co., Philadelphia, Pa.) suitably modified so that the tablets 2 are visible from both sides. The conveyor belt 9 transports the carriers 6 and hence tablets 2 past two sets of photoelectric detection means 12 such as two-dimensional Charge Couple Device (CCD) cameras. Two-dimensional CCD cameras provide superior resolution and result in a more efficient, less complex system in comparison to one-dimensional CCD cameras Suitable Cameras are Videk 256×256 High Speed Cameras available from Videk Inc. (Canandaigua, N.Y.).

According to FIG. 2, each set of cameras 12 is positioned on opposing sides of a separate tablet 2 enabling the simultaneous inspection of both faces of two tablets 2. Proper camera placement aids in ensuring that both sets of cameras do not capture the image of the same tablet 2. Preferably the cameras 12 are separated by an even number of carriers 6. As a consequence of the separation if the carriers are split into two groups (odd and even), one pair of cameras is inspecting an odd tablet carrier 6 while the other pair is inspecting an even tablet carrier 6. To avoid having the same tablet 2 inspected twice, one image is captured for every two carriers that pass the sensor 18 described below. This effectively doubles the maximum inspection rate of the vision system. Typically, the images may be merged into one video signal with a merging means such as a frame merger. An exemplary frame merger is a Videk Electronic Prism available from Videk Inc. (Canandaigua, N.Y.).

An alternative photoelectric means 12 comprise four optic fibers connected to one or more two-dimensional CCD cameras. The four optic fibers are positioned to capture the four images (e.g., both sides of two tablets 2). In yet another embodiment the four cameras may be replaced by an optic arrangement (e.g., series of mirrors and/or prisms) that transmit the desired images to one or more CCD cameras.

Lighting means 15 are positioned to illuminate each tablet face as it is inspected. Proper lighting is important to ensure the quality and consistency of the inspections. Thus, it is preferable to have a light means 15 that provides even, consistent, intense illumination. In addition, the illumination is typically strobed to provide a still or frozen image for the camera to capture, so the image is not distorted.

According to FIGS. 3 and 3A, exemplary light means 15 comprises a fiber optic light source (i.e., light source, wave guide and lighting head). The fibers are contained within an annulus 303. The wave guide fibers are disposed circumferentially about the annulus 303. The fiber ends are spaced about said annulus 303 and project through (but not beyond the surface 312 of the annulus) a slit 306 that circumvents the annulus 306. Preferably the slit 306 is bounded by a mirrored diverter wall 309. The mirrored diverter wall 309 is disposed outside the slit 306 and extends outward from the surface 312 of the plane of the annulus 303 in order to divert and concentrate the light on the desired tablet surface. Preferably, relative to the plane of the surface 312 the diverter wall 309 has an angle of between 45 degrees and 90 degrees. Preferably the angle is as close to 45 degrees as possible yet still provides sufficient illumination of the desired tablet surface area. It is especially preferred that the angle is between 45 degrees and about 65 degrees as this aids in concentrating the light. For the applications that this system is particularly suited for (the detection of small laser drilled holes), the above described lighting when positioned appropriately floods the surface of the tablet with light, causing the laser hole to appear as a dark shadow. An exemplary optic fiber light head was made by Fostec, Inc. (Auburn, N.Y.).

According to FIG. 1 a sensor means 18 is conveniently located to detect the passage of the conveyor means 9 (and thus tablet movement). The sensor 18 coordinates tablet movement with the camera 12. An exemplary sensor is a Banner SM312CV available from Banner Engineering Corp. (City, Location).

A transducer means 21 is disposed downstream from the cameras 12 and positioned so that in conjunction with a separation means 24, separation or preselected tablets from the carriers 6 can be effected. The transducer means 21 is responsive to a signal which is based on selection criteria that is applied to the photo images as described above. An exemplary transducer means 21 and separation means 24 is a solenoid connected to an air ejector. An alternative separation means 24 is a pivotable arm or reciprocating member. An alternative transducer means 21 is a bimetallic strip that deflects when charged. An exemplary pivotable arm system includes a H-2073-027 diverter solenoid available from Lucas Ledex Inc. (Vandalia, Ohio).

The separation means 24 diverts preselected tablets to a chute 27 positioned to receive those tablets and the remaining tablets are transported in the tablet carriers 6 by conveyor 9 to a suitable receptacle 30.

FIG. 4 schematically depicts the photoimage processing and signal processing aspects of this invention. According to FIG. 4 the photoimages are collected by a plurality of photodetection means 401 and merged electronically into a single videosignal by a frame merger 404. The single signal is processed at a first signal processor 407; for example, a VIDEK RM1000 Vision System signal processor available from the Videk Inc. (Canandaigua N.Y.).

The signal processor 407 analyzes the tablets based on the number and intensity of dark pixels detected on the tablet surface within predetermined inspection areas defined for each camera. The particular CCD cameras used (described above) supply 256 different levels of light intensity varying from black (0) to white (255) typically referred to as the gray scale. For the application that this system is particularly suited for (the detection of small laser drilled holes), the following analysis is performed. However, other analyses may be utilized and are within the scope of this invention. The analysis is based on two criteria for each camera. One criteria identifies the front or back of the tablet and the other criteria identifies the presence of a laser drilled hole (in an exemplary application the hole is approximately 0.55 to 0.65 mm. in diameter and approximately 6 mm. deep). The criteria are based on the number and intensity of pixels detected by the camera. A pixel is the smallest resolveable light sensitive element of a sensor. The system determines if each camera is detecting the front (few dark pixels) or the back (many dark pixels) and if the camera detects the laser hole (minimum number dark pixels is less than or equal to the number of measured dark pixels which is less than or equal to the maximum number of dark pixels). The above identifications are made by comparing the digitized camera output signals to predetermined standards (i.e., parameters) whose selection is described below.

The front/back standard may be selected by passing a number of tablets through the vision system and determining the average light intensity (i.e., the average gray scale, (i.e., the sum of the gray scale values of the number of pixels having a gray scale value greater than or equal to zero divided by the number of pixels having a gray scale value greater than or equal to zero)) for both sides of the tablet. The absolute value of the difference of the two averages is divided by two and added to the lower average number to obtain the threshold standard for back/front comparisons. Thus the signal processor 407 compares the digitized camera output signals to this threshold standard and produces a resultant output signal. The resultant output signals, that correspond to an average gray scale value that is equal to or below that threshold standard, correspond to an image of the darker side of the tablet. Those resultant output signals, that correspond to an average gray scale value that is above that threshold standard, correspond to an image of the lighter side of the tablet.

The hole/no-hole standard may be selected by passing a number of tablets through the vision system to determine the definition of a dark pixel (intensity). This definition may correspond to the above threshold standard for the distinction between the lighter and darker side described above. This threshold standard may be iteratively adjusted as desired by comparing the actual presence of a tablet hole to the system values during a sample run. Then a lower and upper limit is selected for the number of those dark pixels. This may be accomplished by iteratively adjusting the lower and upper limits based on comparisons of sample data for the hole/no-hole parameter and the actual presence of a hole during a sample run. The limits are preferably adjusted to bound only those tablets that actually have a hole. Thus, the signal processor 407 compares signals to these three parameters and produces a resultant output signal. Those resultant signals, that correspond to a number of pixels outside of the lower and upper limits, correspond to anything other than the presence of a shadow (e.g., hole). Those resultant signals that correspond to a number of pixels between the lower and upper limits correspond to the presence of a shadow (e.g., hole).

The signal processor 407 produces an output signal based on the above comparisons. For each face of the tablet the signals correspond to, for example, $D\phi=1$ front, or $D\phi=0$ back, and $D1=1$ hole, or $D1=0$ no hole. A second signal processor 410 receives those signals from the first signal processor and compares them to preselected signals. Only when signals corresponding to $D\phi=1$ front and $D1=1$ hole for one tablet side and $D\phi=0$ back and $D1=0$ no hole for the other tablet side are received is a tablet selection output signal transmitted for tablet selection. The output selection signal is transmitted to the transducer 414 which is normally in the "reject product" position and must be energized by a signal from the second signal processing means 410 to move to the "good product" position. Thus, all product is normally rejected and must be actively accepted. This increases the accuracy of the quality control system. For example, in case of a solenoid failure this positive acceptance of good product ensures that all tablets will fail, maintaining the quality control.

This vision system and method makes a significant advance in the art by providing a simple, fast, direct check of the presence of a hole or other surface feature of a pharmaceutical tablet.

It should be understood that the invention is not limited to the particular embodiments shown and described herein, but that various changes and modifications may be made without departing from the spirit and scope of this novel concept as defined by the following claims.

I claim:

1. A visual inspection system particularly adapted for inspecting pharmaceutical tablets comprising:
   a. a first pair of two-dimensional charge couple device photoelectric detection means positioned for detecting the light intensity within predetermined inspection areas on opposing sides of a tablet and for generating a detection signal which varies with the light intensity detected by said photoelectric means;
   b. a second pair of two-dimensional charge couple device photoelectric detection means positioned for detecting the light intensity within predetermined inspection areas on opposing sides of a tablet and for generating a detection signal which varies with the light intensity detected by said photoelectric means;
   c. a conveyor means for sequentially presenting tablets to said photoelectric detector means, said first pair and second pair of photoelectric detector means disposed along said conveyor means and said first pair and second pair of photoelectric detector means separated by an even number of tablets;
   d. signal processing means for comparing said detection signals to at least one predetermined standard to generate at least one selection;
   e. transducer means responsive to said selection signal; and
   f. separation means responsive to said transducer means for separating said tablets into at least two groups in accordance with said selection signal.

2. The inspection system of claim 1 wherein said photoelectric detection means additionally comprises a frame merger means for merging the photoelectric detection means output detection signals into one detection signal.

3. The inspection system of claim 2 wherein said separation means comprises:
   a. a chute positioned to receive tablets from said conveyor means; and
   b. an air ejector for diverting preselected tablets through an exit chute.

4. The inspection system of claim 2 additionally comprising a strobed optic fiber light means for illuminating the tablet surface, said light means disposed between said photoelectric detection means and said tablet, said light means including a lighting head which comprises: fibers disposed circumferentially
   a. wave guide fibers disposed circumferentially about an annulus;
   b. wave guide fiber ends spaced about said annulus and projecting through a slit that circumvents said annulus; and
   c. a mirrored diverter wall disposed outside said slit and extending from said annulus.

5. A method for inspecting the surface of pharmaceutical tablets comprising:
   a. simultaneously detecting the light intensity within a predetermined inspection area on opposing sides of a tablet with a photoelectric detection means;
   b. generating detection signals which vary with the light intensity detected in said inspection areas;
   c. comparing the detection signals to a first predetermined standard that corresponds to the presence of a hole disposed on said tablet, a second predetermined standard that corresponds to the tablet front, a third predetermined standard that corresponds to the tablet back and a fourth predetermined standard that corresponds to the absence of a hole on a tablet surface;
   d. generating selection signals each selection signal associated with a comparison; and
   e. receiving said selection signals, corresponding to the tablet front, tablet back, hole, and no hole;
   f. generating a hole selection signal when said selection signals correspond to a table front having a hole and a tablet back not having a hole; and
   g. selectively separating those tablets that have a hole selection signal.

6. The method of claim 5 wherein said output detection signals are merged into a single output detection signal.

7. The method of claim 6 additionally including a second photoelectric detection means and wherein tablets are sequentially presented for detection and two tablets are inspected simultaneously by said first and second photoelectric detection means.

* * * * *

UNITED STATES PATENT AND TRADEMARK OFFICE
CERTIFICATE OF CORRECTION

PATENT NO. : 5,085,510

DATED : February 4, 1992

INVENTOR(S) : William H. Mitchell

It is certified that error appears in the above-identified patent and that said Letters Patent is hereby corrected as shown below:

Column 6, line 10 insert "signal" after "selection".

Column 6, line 30 after "comprises" delete "fibers disposed circumferentially".

Signed and Sealed this

First Day of June, 1993

Attest:

MICHAEL K. KIRK

Attesting Officer

Acting Commissioner of Patents and Trademarks